(12) United States Patent
Ishii et al.

(10) Patent No.: US 8,758,854 B2
(45) Date of Patent: Jun. 24, 2014

(54) PROCESS FOR PRODUCING SUGAR-PLUM-SHAPED PARTICLE

(75) Inventors: Masanori Ishii, Gunma (JP); Keisuke Shiraishi, Gunma (JP)

(73) Assignee: Nikko Rica Corporation (JP)

(*) Notice: Subject to any disclaimer, the term of this patent is extended or adjusted under 35 U.S.C. 154(b) by 573 days.

(21) Appl. No.: 12/937,017

(22) PCT Filed: Aug. 27, 2008

(86) PCT No.: PCT/JP2008/002321
§ 371 (c)(1),
(2), (4) Date: Oct. 8, 2010

(87) PCT Pub. No.: WO2009/130745
PCT Pub. Date: Oct. 29, 2009

(65) Prior Publication Data
US 2011/0034615 A1 Feb. 10, 2011

(30) Foreign Application Priority Data
Apr. 25, 2008 (JP) .................. 2008-115723

(51) Int. Cl.
C08L 83/04 (2006.01)
C08L 77/00 (2006.01)

(52) U.S. Cl.
USPC ........... 427/220; 427/222; 524/506; 524/500; 524/538

(58) Field of Classification Search
USPC .................. 427/220, 222; 524/506, 500, 538
See application file for complete search history.

(56) References Cited

U.S. PATENT DOCUMENTS 7,652,091 B2 * 1/2010 Inokuchi ................ 524/474

FOREIGN PATENT DOCUMENTS

| JP | 9-208644 | | 8/1997 |
| JP | 11-293113 | | 10/1999 |
| JP | 2000-212442 | | 8/2000 |
| JP | 212442 | * | 8/2000 |
| JP | 2000-239396 | | 9/2000 |
| JP | 038049 | * | 2/2002 |

OTHER PUBLICATIONS

Ahmed et al., Determination of Descriptors for Organosilicon Compounds by Gas Chromatography and Non-Aqueous Liquid-Liquid Partitioning, 2007, Science Direct, Journal of Chromatography A, p. 179-192.*

* cited by examiner

Primary Examiner — Timothy Meeks
Assistant Examiner — Ann Disarro
(74) Attorney, Agent, or Firm — Gerald E. Hespos; Michael J. Porco; Matthew T. Hespos

(57) ABSTRACT

To obtain a sugar-plum shaped composite particle, a reaction vessel with 300 parts by weight of water placed therein is charged with 30 parts by weight of polymethyl methacraylate resin particles of 2 μm average particle diameter, and ultrasonic waves are applied to the mixture for 1 minute to obtain a particle dispersion liquid. Subsequently, 15 parts by weight of methyltrimethoxysilane is added to the dispersion liquid to obtain methyltrimethoxysilane hydrolyzates in the dispersion liquid. Thereafter, 10 parts by weight of 1 weight % aqueous ammonia is added thereto and agitated. One minute later, the agitation is discontinued, and the mixture is allowed to stand still for 10 hours to effect maturation. The resultant mixture is filtered and dried to obtain sugar-plum-shaped particles provided on their surfaces with polyorganosiloxane projections.

6 Claims, 12 Drawing Sheets

| SAMPLE | EXAMPLE 8 | COMPARATIVE EXAMPLE 2 |
|---|---|---|
| D VALUE | 23.45 | 26.13 |
| SPECULAR REFLECTION | 1.303 | 1.676 |
| RETROREFLECTION | 1.851 | 2.956 |

D VALUE : REFLECTED LIGHT INTENSITY AT 0° ANGLE
SPECULAR REFLECTION : MAXIMUM REFLECTED LIGHT INTENSITY/D VALUE AT SPECULAR REFLECTION SIDE
RETROREFLECTION : MAXIMUM REFLECTED LIGHT INTENSITY/D VALUE AT INCIDENT LIGHT SIDE

PROCESS FOR PRODUCING SUGAR-PLUM-SHAPED PARTICLE

BACKGROUND OF THE INVENTION

1. Field of the Invention

The present invention relates to a process for producing composite particles formed by coating organic resin particles mainly with polyorganosiloxane, and particularly relates to a process for producing sugar-plum-shaped particles having projections mainly of the polyorganosiloxane on surfaces of the composite particles.

2. Description of the Related Art

The sugar-plum-shaped particles of the present invention are used as an agent for slidability, wear resistance, antiblocking, water repellency, light diffusivity, etc., to various plastics and rubbers, and cosmetic products, etc.

Polyorganosiloxane particles are widely used for wear resistance, slidability, light diffusivity, anti-blocking and the like of various plastics and rubbers, etc. In particular, particles are preferred with a spherical shape and an average particle diameter of 0.1 to 10 μm.

To improve functionality, a proposed process produces composite particles containing polyorganosiloxane. For example, alkoxysilane is added into a system in which silica, alumina, etc. are dispersed as core particles, thereby obtaining composite particles on which a polyorganosiloxane coating is formed (see JP 2000-212442).

A process is disclosed to provide composite particles formed such that organic resin particles are coated with polyorganosiloxane (see JP 2000-239396).

SUMMARY OF THE INVENTION

Various organic resin particles of acrylic, polyurethane, polystyrene, polyamide, etc. are used as additives for various plastics and rubbers, etc., and raw materials for cosmetic products.

These organic resin particles are restricted in usage environment because heat-resistance is low and the particles are prone to be cohesive with each other with temperatures. The organic resin particles also are inferior in fluidity, difficult to handle, and difficult to disperse uniformly in various plastics and rubbers and the like.

The composite particles disclosed in Patent Document 2 are formed by coating various organic resin particles with polyorganosiloxane, which improves fluidity to a certain degree, but is far from being adequate. The composite particles synthesized in Patent Document 2 also are spherical particles whose surfaces are coated uniformly with polyorganosiloxane, which are inadequate for optical features such as light diffusivity.

The inventors of the present invention found that fluidity was substantially improved in comparison to the above-mentioned spherically-shaped coated particles, and optical features were also significantly improved in comparison to other conventional materials, when composite particles were formed such that polyorganosiloxane was coated on various organic resin particles as core particles with a 0.1 μm to 50 μm average particle diameter of the composite particles, which were sugar-plum-shaped and have protrusions on surfaces of the composite particles. The inventors thus completed the present invention.

In particular, the present invention, which will further be described below, relates to sugar-plum-shaped particles that are composite particles formed by coating polyorganosiloxane and have polyorganosiloxane projections on the surfaces of the composite particles, and to a process for producing the composite particles.

A first aspect of the present invention provides a process for producing sugar-plum-shaped particles in which organotrialkoxysilane and/or an organotrialkoxysilane hydrolysate as a main component compound, organic resin particles that are dispersed, and an alkaline substance or an alkaline aqueous solution are added into a reaction system before the main component compound undergoes a dehydration condensation reaction, and polyorganosiloxane projections are precipitated on surfaces of the organic resin particles through a dehydration condensation reaction of the main component compound.

A second aspect of the present invention provides the process for producing the sugar-plum-shaped particles according to the first aspect, wherein at least one of triorganomonoalkoxysilane, diorganodialkoxysilane, tetraalkoxysilane, and organohalosilane can be selected and added as an accessory component compound.

A third aspect of the present invention provides the process for producing the sugar-plum-shaped particles according to the first or second aspect, wherein the alkaline substance or the alkaline aqueous solution is added into a mixed liquid of the dispersed organic resin particles and at least the main component compound.

A fourth aspect of the present invention provides the process for producing the sugar-plum-shaped particles according to the first or second aspect, wherein at least the main component compound is added into a mixed liquid of the dispersed organic resin particles and the alkaline substance or the alkaline aqueous solution.

A fifth aspect of the present invention provides the process for producing the sugar-plum-shaped particles according to the fourth aspect, wherein when at least the main component compound is water-insoluble, a hydrolysis reaction progresses at an interface of two separated layers in a reaction liquid, and a hydrolysate that has become water-soluble by the progress of the hydrolysis reaction dissolves to a dispersion liquid to undergo a dehydration condensation reaction.

A sixth aspect of the present invention provides the process for producing the sugar-plum-shaped particles according to any one of the first to fifth aspects, wherein a ratio of the organic resin particles and the polyorganosiloxane is 10 to 100 parts by weight of the polyorganosiloxane relative to 100 parts by weight of the organic resin particles, and a pH of the reaction liquid is 8.0 to 10.5 during the dehydration condensation reaction.

A seventh aspect of the present invention provides the process for producing the sugar-plum-shaped particles according to any one of the first to sixth aspects, wherein the organic resin particles are resin particles of acrylic, polyurethane, polystyrene or polyamide, and/or copolymer or composite particles of these organic resins.

According to various aspects of the present invention, the sugar-plum-shaped composite particles, which are formed by coating polyorganosiloxane on the organic resin particles and have the polyorganosiloxane projections on the composite particle surfaces, can be produced efficiently through an industrially advantageous process.

DETAILED DESCRIPTION OF THE PREFERRED EMBODIMENTS

Figure 1:
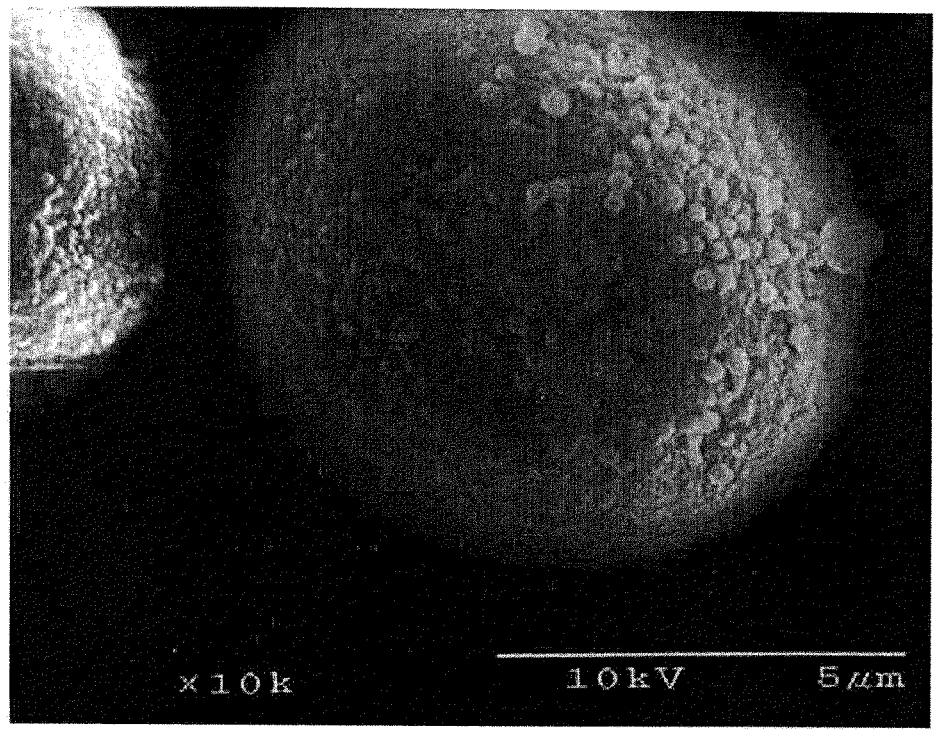
FIG. 1 is an electron micrograph of composite particles as obtained in Example 1.

The present invention will be described in detail below.

Sugar-plum-shaped particles of the present invention can be obtained in a process of hydrolyzing and dehydration-condensing organotrialkoxysilane as a main component compound where organic resin particles are added in a reaction system before the main component compound undergoes a dehydration condensation so as to precipitate polyorganosiloxane on surfaces of the organic resin particles.

The organic resin particles are particularly made up of a resin of acrylic, polyurethane, polystyrene, polyamide, phenol or melamine, or composite or copolymer resin particles containing any of the above resins.

The organic resin particles as used in the present invention can be organic resin particles obtained through a general production process. An average particle diameter and a particle size distribution thereof may not particularly be restricted, but appropriately selected for a desired use or application.

No restriction is made as to whether a crosslinking should exist in the organic resin particles.

A shape of the organic resin particles may not particularly be restricted as long as they are substantially spherical like a pearl, a potato, a microparticle aggregate and the like.

The spherical resin particles as used in the present invention mean resin particles that are dried or dispersed in a solvent in advance.

An additive amount of the spherical resin particles as used in the present invention is set to be 1 to 50 parts by weight relative to 100 parts by weight of a reaction liquid. A yield per unit volume may be inferior if an additive amount of the spherical resin particles is less than or equal to 1 part by weight. The particles may not be taken out as sugar-plum-shaped particles because the particles tend to be aggregated with each other if an additive amount of the spherical resin particles is more than or equal to 50 parts by weight.

An initial reaction liquid and a dispersant for the organic resin particles as used in the present invention is water with a conductivity less than or equal to 500 µS/cm or a mixture of such water and a water-soluble organic solvent.

The water-soluble organic solvent may not particularly be restricted as long as it is water-soluble and inert to organotrialkoxysilane as a main component compound, a triorganomonoalkoxysilane; diorganodialkoxysilane; tetraalkoxysilane; or organohalosilane as an accessory component compound, and any of the various spherical resin particles. Nevertheless, a lower alcohol may be preferred because it is easier to obtain.

A mixture ratio of the water and the water-soluble organic solvent is preferably less than or equal to 1 part by weight of the water-soluble organic solvent relative to 1 part by weight of the water.

A process for dispersing the spherical resin particles may not particularly be restricted as long as the spherical resin particles are dispersed. Nevertheless, a ultrasonic dispersion may be preferred.

If hydrophobic resin particles are used, it is preferable to disperse such particles in the water-soluble organic solvent in advance.

Organotrialkoxysilane as the main component compound of the present invention is indicated by the general formula:

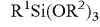

wherein $R^1$ represents a univalent organic group having at least one methyl group, ethyl group, propyl group, butyl group or other linear or branched alkyl group, phenyl group, amino group, epoxy group, or vinyl group with 1 to 6 carbons; and $R^2$ represents a linear or branched alkyl group with 1 to 6 carbons, which is the same as $R^1$.

More specifically, examples of organotrialkoxysilane are methyltrimethoxysilane, methyltriethoxysilane, methyltri-n-propoxysilane, methyltri-i-propoxysilane, methyltri-n-butoxysilane, methyltri-i-butoxysilane, methyltri-s-butoxysilane, methyltri-t-butoxysilane, ethyltrimethoxysilane, n-propyltrimethoxysilane, i-propyltrimethoxysilane, n-butyltrimethoxysilane, s-butyltrimethoxysilane, t-butyltrimethoxysilane, N-β(aminoethyl)γ-aminopropyltrimethoxysilane, γ-glycidoxypropyltrimethoxysilane, vinyltrimethoxysilane, phenyltrimethoxysilane, etc.

Such organotrialkoxysilane may be used individually or in a mixture of two or more among the above examples. Nevertheless, methyltrimethoxysilane and phenyltrimethoxysilane are preferred because they are easier to obtain.

An additive amount of organotrialkoxysilane as used in the present invention is preferably 10 to 100 parts by weight of polyorganosiloxane relative to 100 parts by weight of the organic resin particles. Projections tend to be more difficult to form if an additive amount is less than or equal to 10 parts by weight. Particles of polyorganosiloxane alone tend to form easily if an additive amount exceeds 100 parts by weight.

The present invention can adopt any synthesis process as long as polyorganosiloxane projections are precipitated on surfaces of the organic resin particles through a dehydration condensation reaction of the main component compound by adding the main component compound, the organic resin particles, and an alkaline substance or an alkaline aqueous solution into a reaction system before the main component compound undergoes a dehydration condensation reaction. Particularly, a first synthesis process produces sugar-plum-shaped particles by adding the alkaline substance or the alkaline aqueous solution into a liquid in which the dispersed organic resin particles and at least the main component compound are mixed. More specifically, this synthesis process includes the steps of:

A) obtaining at least a hydrolysate of the main component compound by adding at least the main component compound into a system in which the spherical resin particles have been dispersed in water or a mixed liquid of water and an aqueous organic solvent and stirring the dispersion; and B) precipitating the hydrolysate as the polyorganosiloxane on surfaces of the spherical resin particles by adding the alkaline substance or the alkaline aqueous solution to the hydrolysate of the main component compound so as to perform a dehydration condensation of, at least, the hydrolysate of the main component compound.

Particularly, a second synthesis process produces sugar-plum-shaped particles by adding at least the main component compound into a liquid in which an organic resin particle dispersion liquid and the alkaline substance or the alkaline aqueous solution are mixed. This synthesis process includes a case in which at least the main component compound is water-insoluble, a hydrolysis reaction progresses at an interface of two separated layers in a reaction liquid, and a hydrolysate that has become water-soluble through the progress of the hydrolysis reaction dissolves to a dispersion liquid so to undergo a dehydration condensation reaction.

Particularly, a third synthesis process produces sugar-plum-shaped particles by simultaneously adding the alkaline substance or the alkaline aqueous solution and at least the main component compound into an organic resin particle dispersion liquid. These processes can be carried out by employing the above-described first process.

A process for adding at least the main component compound may not particularly be restricted, and the process may be performed through a short time loading or a continuous dripping.

Examples of the alkaline substance are hydroxide, oxide, and carbonate of metals of groups IA and IIA of the periodic table, or organic nitrogen compounds, ammonia, etc. The alkaline aqueous solution means an aqueous solution of any of the above alkaline substances. Nevertheless, ammonia is especially preferred because it is easier to eliminate after reaction. Any of the alkaline substances and/or the aqueous solution thereof may be used solitarily or by mixture of two or more kinds. Further, the alkaline aqueous solution may be used even if it contains a water-soluble organic solvent, a surfactant, etc.

The alkaline substance or the alkaline aqueous solution is preferably added such that a pH level of the reaction liquid is within a range of 8.0 to 10.5 during the dehydration condensation reaction of the main component. If a pH of the reaction liquid is less than or equal to 8.0, then the particles tend to be cohesive with each other. If a pH of the reaction liquid exceeds 10.5, then the dehydration condensation reaction proceeds so quickly that projections are difficult to form on surfaces of the organic resin particles, with resultant simple spherical composite particles on which polyorganosiloxane is uniformly coated.

A reaction liquid temperature of 10 to 60° C. is preferred to perform the dehydration condensation of the hydrolysate of the main component compound by adding the alkaline substance or the alkaline aqueous solution.

Preferably, the alkaline substance or the alkaline aqueous solution is added quickly while the reaction liquid is stirred. The stirring of the reaction liquid when the alkaline substance or the alkaline aqueous solution is added may not particularly be restricted. However, a mild stirring is usually preferred to some degree that the liquids are mixed because the particles tend to be cohesive with each other or shaped irregularly under an intensive stirring.

To carry out the present invention, at least one of triorganomonoalkoxysilane, diorganodialkoxysilane, tetraalkoxysilane, and organohalosilane may be selected and added as an accessory component compound to the above-described organotrialkoxysilane as the main component compound.

Examples of triorganomonoalkoxysilane are trimethylmonomethoxysilane, trimethylmonoethoxysilane, trimethylmono-n-propoxysilane, trimethylmono-i-propoxysilane, trimethylmono-n-butoxysilane, trimethylmono-i-butoxysilane, trimethylmono-s-butoxysilane, trimethylmono-t-butoxysilane, triethylmonomethoxysilane, tri-n-propylmonomethoxysilane, tri-i-propylmonomethoxysilane, tri-n-butylmonomethoxysilane, tri-s-butylmonomethoxysilane, tri-t-butylmonomethoxysilane, tri-N-β(aminoethyl)γ-aminopropylmonomethoxysilane, tri-γ-glycidoxypropylmonomethoxysilane, trivinylmonomethoxysilane, triphenylmonomethoxysilane, etc.

Examples of diorganodialkoxysilane are dimethyldimethoxysilane, dimethyldiethoxysilane, dimethyldi-n-propoxysilane, dimethyldi-i-propoxysilane, dimethyldi-n-butoxysilane, dimethyldi-i-butoxysilane, dimethyldi-s-butoxysilane, dimethyldi-t-butoxysilane, diethyldimethoxysilane, di-n-propyldimethoxysilane, di-i-propyldimethoxysilane, di-n-butyldimethoxysilane, di-s-butyldimethoxysilane, di-t-butyldimethoxysilane, di-N-β(aminoethyl)γ-aminopropyldimethoxysilane, di-γ-glycidoxypropyldimethoxysilane, divinyldimethoxysilane, diphenyldimethoxysilane, etc.

Examples of tetraalkoxysilane are tetramethoxysilane, tetraethoxysilane, tetra-n-propoxysilane, tetra-i-propoxysilane, tetra-n-butoxysilane, tetra-i-butoxysilane, tetra-s-butoxysilane, tetra-t-butoxysilane, etc.

Examples of organohalosilane are methyltrichlorosilane, dimethyldichlorosilane, trimethylmonochlorosilane, ethyltrichlorosilane, diethyldichlorosilane, triethylmonochlorosilane, etc.

In the present invention, the organotrialkoxysilane and/or the hydrolysate of the organotrialkoxysilane as the main component compound is/are dehydration-condensed under the presence of the alkaline substance or the alkaline aqueous solution. In this case, a polyorganosiloxane layer on the sugar-plum-shaped particles that have been synthesized can grow when the organotrialkoxysilane and/or the hydrolysate of the organotrialkoxysilane is/are dehydration-condensed further in a reaction liquid slurry in which the dehydration condensation has been carried out.

As to a speed for adding the main component compound in this case, a gradual drip is preferred because particles of the polyorganosiloxane alone tend to form when the speed is too high.

The particles thus synthesized are subsequently subject to separation by filtration, rinsing with water or an organic solvent, drying, and crushing when necessary, to obtain microparticles.

The obtained particles are sugar-plum-shaped particles with the polyorganosiloxane projections on the particles surfaces. Sizes in both height and width directions of the projections of the sugar-plum-shaped particles are 1/50 to 1/2 of the core particle diameter. The projections are formed all over more than or equal to a half of the entire surface of the core particles.

The surfaces may be treated by adding various silane coupling agents and the like into the reaction system after the sugar-plum-shaped polyorganosiloxane are synthesized through the dehydration condensation reaction as described above.

Examples and comparative examples will be described blow, and the present invention is not restricted by the examples.

Example 1

Three hundred parts by weight of water were charged into a reaction vessel equipped with a thermometer, a reflux device and a stirrer, and loaded thereinto were 22.5 parts by weight of polyurethane spherical resin particles with an average particle diameter of 7 μm ("Art Pearl C-800" (transparent) made by Negami Chemical Industrial Company). Ultrasonic waves were irradiated for 1 minute to obtain a polyurethane resin particle dispersion liquid.

A liquid temperature of the dispersion liquid was set to be 30° C., and further added were 15 parts by weight of methyltrimethoxysilane to obtain a hydrolysate of methyltrimethoxysilane in the polyurethane resin particle dispersion liquid.

A 30-minute stirring was carried out by keeping the 30-degree Celsius liquid temperature, and quickly added were 10 parts by weight of 1 weight percent ammonia water. The stirring was stopped in 1 minute. A pH of such reaction liquid was 9.7 at this time.

Maturation was done for 2 hours in a still standing state, filtration and drying were carried out, and white powders were obtained. The obtained white powders were 28.8 grams.

By raw material charge ratios, polymethylsilsesquioxane was 33 parts by weight relative to 100 parts by weight of the polyurethane resin particles.

The obtained powders were observed under an electron microscope. The photograph of FIG. 1 shows sugar-plum-shaped particles having projections on surfaces of the particles. Particles of polymethylsilsesquioxane alone were hardly observed.

Sizes of 100 projections among the projections of the obtained particles were measured to see a height of 0.2 μm from the core particle and a width of 0.3 μm in average.

The Art Pearl C-800 as the core particles and the obtained composite particles of Example 1 were measured with a thermogravity differential thermal balance ("TG-DTA", TG8120 made by Rigaku Corporation). A weight reduction of the Art Pearl C-800 in a transition from 200 to 445° C. was 76.7 weight percent, whereas a weight reduction of the obtained composite particles of Example 1 in a transition from 200 to 445° C. was 69.8 weight percent.

The Art Pearl C-800 and the obtained sugar-plum-shaped particles of Example 1 were heat-treated at 150° C. Fluidity was lost in the Art Pearl C-800 because the particles were cohesive with each other. Such cohesion was not observed in the obtained sugar-plum-shaped particles of Example 1, which maintained fluidity similar before the heat treatment. Another heat treatment was subsequently carried out at 200° C. Again, such cohesion was not observed in the obtained sugar-plum-shaped particles of Example 1, which maintained fluidity similar before the heat treatment. The results appear to indicate the heat resistance was improved because of coating by the polyorganosilsesquioxane.

Examples 2 to 7

Sugar-plum-shaped particles were obtained as in Examples 2 and 3 in the same manner as in Example 1 in addition to reaction temperatures as shown in Table 1 below.

Sugar-plum-shaped particles were obtained as in Examples 4 and 5 in the same manner as in Example 1 in addition to charging amounts as shown in Table 1 below.

Sugar-plum-shaped particles were obtained as in Examples 6 and 7 in the same manner as in Example 1 in addition to average particle diameters of spherical polyurethane particles and charging amounts as shown in Table 1 below.

TABLE 1

|  | Example 2 | Example 3 | Example 4 | Example 5 | Example 6 | Example 7 |
| --- | --- | --- | --- | --- | --- | --- |
| Water (part by wt.) | 300 | 300 | 300 | 300 | 300 | 300 |
| Organic resin particles | C-800 | C-800 | C-800 | C-800 | C-400 | Polyurethane |
| Average particle diameters (μm) of organic resin particles | 7 | 7 | 7 | 7 | 14 | 2 |
| Additive amount of organic resin particles (part by wt.) | 22.5 | 22.5 | 25 | 33 | 40 | 18 |
| Methyltrimethoxysilane (part by wt.) | 15 | 15 | 24 | 6 | 12 | 8 |
| Reaction temperatures during dehydration condensation (° C.) | 55 | 20 | 30 | 30 | 30 | 20 |
| 1 weight % ammonia water (part by wt.) | 10 | 10 | 10 | 10 | 10 | 10 |
| Shape of synthesized particles | Sugar-plum-shaped | Sugar-plum-shaped | Sugar-plum-shaped | Sugar-plum-shaped | Sugar-plum-shaped | Sugar-plum-shaped |
| Width of projections (μm) | 0.2 | 0.4 | 0.5 | 0.1 | 0.3 | 0.2 |
| Average particle diameters of synthesized particles (μm) | 7.3 | 7.4 | 7.9 | 7.6 | 9.1 | 2.1 |

Example 8

Three hundred parts by weight of water were charged into a reaction vessel equipped with a thermometer, a reflux device and a stirrer, and loaded thereinto were 30 parts by weight of polymethylmethacrylate resin particles with an average particle diameter of 2 μm ("Art Pearl J-4P" made by Negami Chemical Industrial Company). Ultrasonic waves were irradiated for 1 minute to obtain a polymethylmethacrylate resin particle dispersion liquid.

A liquid temperature of the dispersion liquid was set to be 30° C., and further added were 15 parts by weight of methyltrimethoxysilane to obtain a hydrolysate of methyltrimethoxysilane in the polymethylmethacrylate resin particle dispersion liquid.

A 30-minute stirring was carried out by keeping the 30-degree Celsius liquid temperature, and quickly added were 10 parts by weight of 1 weight percent ammonia water. The stirring was stopped in 1 minute. A pH of such reaction liquid was 9.6 at this time.

Maturation was done for 10 hours in a still standing state, filtration and drying were carried out, and white powders were obtained. By raw material charge ratios, polymethylsilsesquioxane was 25 parts by weight relative to 100 parts by weight of the polymethylmethacrylate resin particles.

Figure 2:
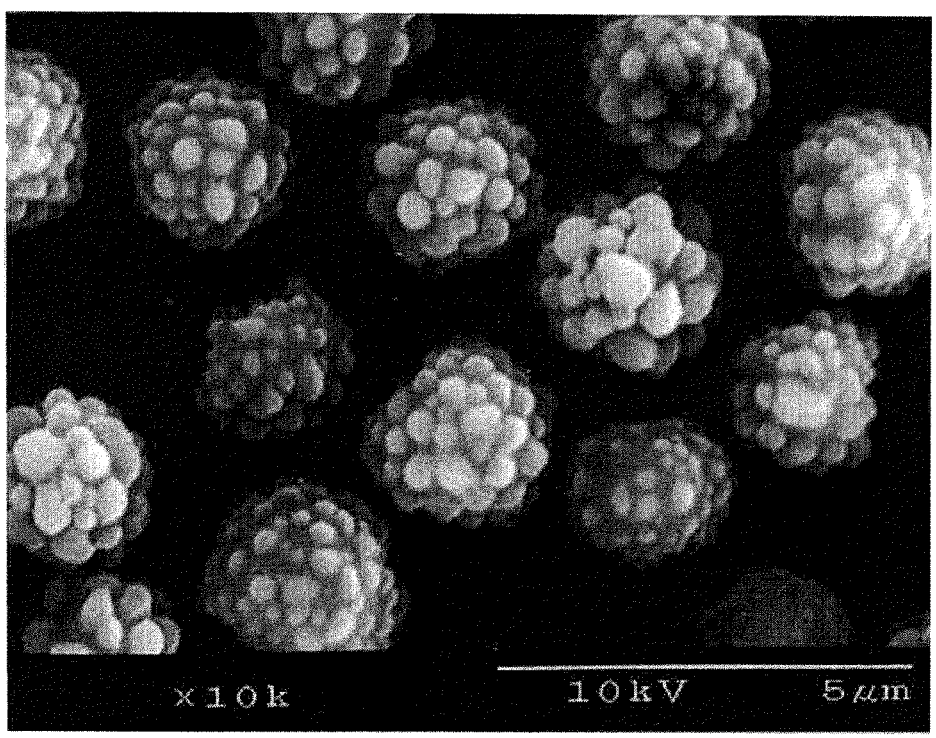
FIG. 2 is an electron micrograph of composite particles as obtained in Example 8.

The obtained white powders were 29.1 grams and observed under an electron microscope. The photograph of FIG. 2 shows sugar-plum-shaped particles having projections on surfaces of the particles. Particles of polymethylsilsesquioxane alone were hardly observed.

Sizes of 100 projections among the projections of the obtained particles were measured to see a height of 0.3 μm from the core particle and a width of 0.5 μm in average The Art Pearl J-4P as the core particles and the obtained composite particles of Example 8 were measured by TG-DTA. A weight reduction of the Art Pearl J-4P in a transition from 200 to 445° C. was 100 weight percent, whereas a weight reduction of the obtained composite particles of Example 8 was 92 weight percent.

The Art Pearl J-4P and the obtained sugar-plum-shaped particles of Example 8 were heat-treated at 150° C. Fluidity was lost in the Art Pearl J-4P because the particles were cohesive with each other. Such cohesion was not observed in obtained sugar-plum-shaped particles of Example 8, which maintained fluidity similar before the heat treatment. Another heat treatment was subsequently carried out at 200° C. Again, such cohesion was not observed in the obtained sugar-plum-shaped particles of Example 8, which maintained fluidity similar before the heat treatment. The results appear to indicate the heat resistance was improved because of coating by the polyorganosilsesquioxane.

Examples 9 to 16

Sugar-plum-shaped particles were obtained as in Example 9 in the same manner as in Example 1 in addition to reaction temperatures as shown in Table 2 below.

Sugar-plum-shaped particles were obtained as in Examples 10 to 12 in the same manner as in Example 1 in addition to charging amounts as shown in Table 2 below.

Sugar-plum-shaped particles were obtained as in Examples 13 and 14 in the same manner as in Example 1 in addition to average particle diameters of core particles and charging amounts as shown in Table 2 below.

Sugar-plum-shaped particles were obtained as in Examples 15 and 16 in the same manner as in Example 1 in addition to core particles as shown in Table 2 below.

TABLE 2

| | Example 9 | Example 10 | Example 11 | Example 12 | Example 13 | Example 14 | Example 15 | Example 16 |
|---|---|---|---|---|---|---|---|---|
| Water (part by wt.) | 300 | 300 | 300 | 300 | 300 | 300 | 300 | 300 |
| Organic resin particles | J-4P | J-4P | J-4P | J-4P | J-7P | Acrylic | M-100 | M-305 |
| Average particles diameter (μm) of organic resin particles | 2 | 2 | 2 | 2 | 7 | 1 | 6 | 5 |
| Additive amount of organic resin particles (part by wt.) | 30 | 19.5 | 26 | 16 | 30 | 20 | 30 | 30 |
| Methyltrimethoxy-silane (part by wt.) | 15 | 22 | 8 | 28 | 15 | 15 | 15 | 15 |
| Reaction temperatures during dehydration condensation (° C.) | 50 | 20 | 20 | 20 | 30 | 20 | 20 | 20 |
| 1 weight % ammonia water (part by wt.) | 10 | 10 | 10 | 10 | 10 | 10 | 10 | 10 |
| Shape of synthesized particles | Sugar-plum-shaped | Sugar-plum-shaped | Sugar-plum-shaped | Sugar-plum-shaped | Sugar-plum-shaped | Sugar-plum-shaped | Sugar-plum-shaped | Sugar-plum-shaped |
| Width of projections (μm) | 0.3 | 0.5 | 0.2 | 0.6 | 0.2 | 0.3 | 0.3 | 0.3 |
| Average particle diameters of synthesized particles (μm) | 2.2 | 2.5 | 2.3 | 2.9 | 7.2 | 1.2 | 6.3 | 5.3 |

Example 17

Fifty parts by weight of methanol were charged into a reaction vessel equipped with a thermometer, a reflux device and a stirrer, and loaded thereinto were 22.5 parts by weight of polyamide spherical resin particles with an average particle diameter of 5 μm. Ultrasonic waves were irradiated for 1 minute to obtain a polyamide resin microparticle dispersion liquid, and then 250 parts by weight of water were charged to obtain a polyamide spherical resin particle dispersion liquid.

A liquid temperature of the dispersion liquid was set to be 30° C., and further added were 15 parts by weight of methyltrimethoxysilane to obtain a hydrolysate of methyltrimethoxysilane.

A 30-minute stirring was carried out by keeping the 30-degree Celsius liquid temperature, and quickly added were 10 parts by weight of 1 weight percent ammonia water. The stirring was stopped in 1 minute. A pH of such reaction liquid was 9.5 at this time.

Maturation was done for 10 hours in a still standing state, filtration and drying were carried out, and white powders were obtained. By raw material charge ratios, polymethylsilsesquioxane was 33 parts by weight relative to 100 parts by weight of the polyamide resin particles.

Figure 3:
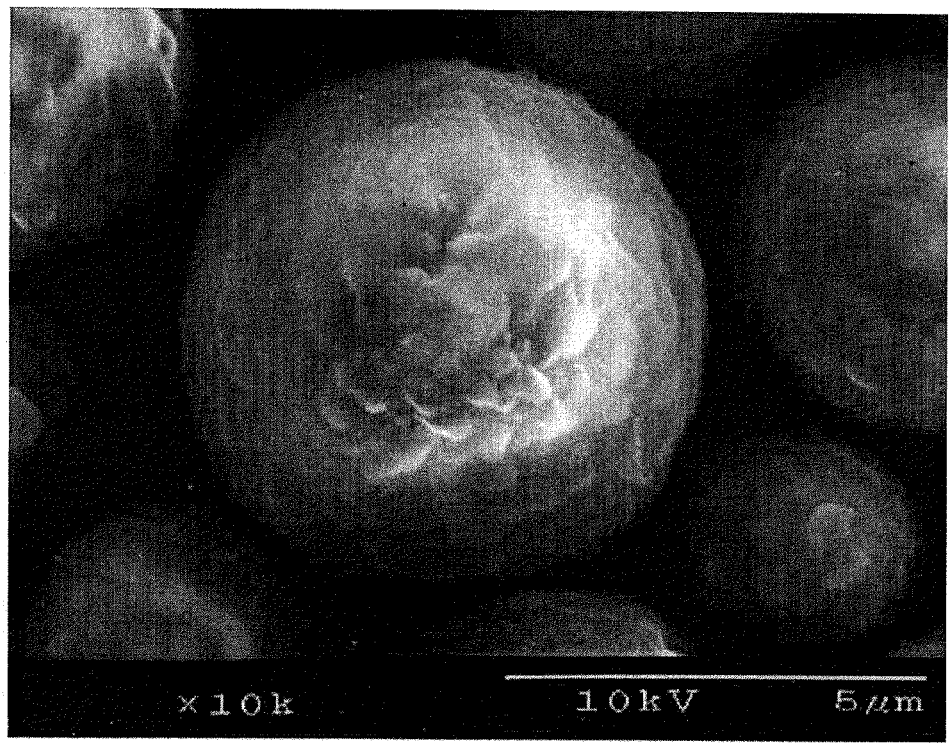
FIG. 3 is an electron micrograph of composite particles as obtained in Example 17.

The obtained white powders were 29.2 grams and observed under an electron microscope. The photograph of FIG. 3 shows sugar-plum-shaped particles having projections on surfaces of the particles. Particles of polymethylsilsesquioxane alone were hardly observed.

The polyamide spherical resin particles as the core particles and the composite particles of Example 17 were measured by TG-DTA. A weight reduction of the polyamide spherical resin particles in a transition from 200 to 445° C. was 76.7 weight percent, whereas a weight reduction of the composite particles of Example 17 was 69.8 weight percent.

Example 18

Three hundred parts by weight of water were charged into a reaction vessel equipped with a thermometer, a reflux device and a stirrer, and loaded thereinto were 25 parts by weight of polystyrene spherical resin particles with an average particle diameter of 1 μm. Ultrasonic waves were irradiated for 1 minute to obtain a polystyrene spherical resin particle dispersion liquid.

A liquid temperature of the dispersion liquid was set to be 30° C., and further added were 20 parts by weight of methyltrimethoxysilane to obtain a hydrolysate of methyltrimethoxysilane.

A 30-minute stirring was carried out by keeping the 30-degree Celsius liquid temperature, and quickly added were 10 parts by weight of 1 weight percent ammonia water. The stirring was stopped in 1 minute. A pH of such reaction liquid was 9.8 at this time.

Maturation was done for 10 hours in a still standing state, filtration and drying were carried out, and white powders were obtained. By raw material charge ratios, polymethylsilsesquioxane was 39 parts by weight relative to 100 parts by weight of the polystyrene resin particles.

Figure 4:
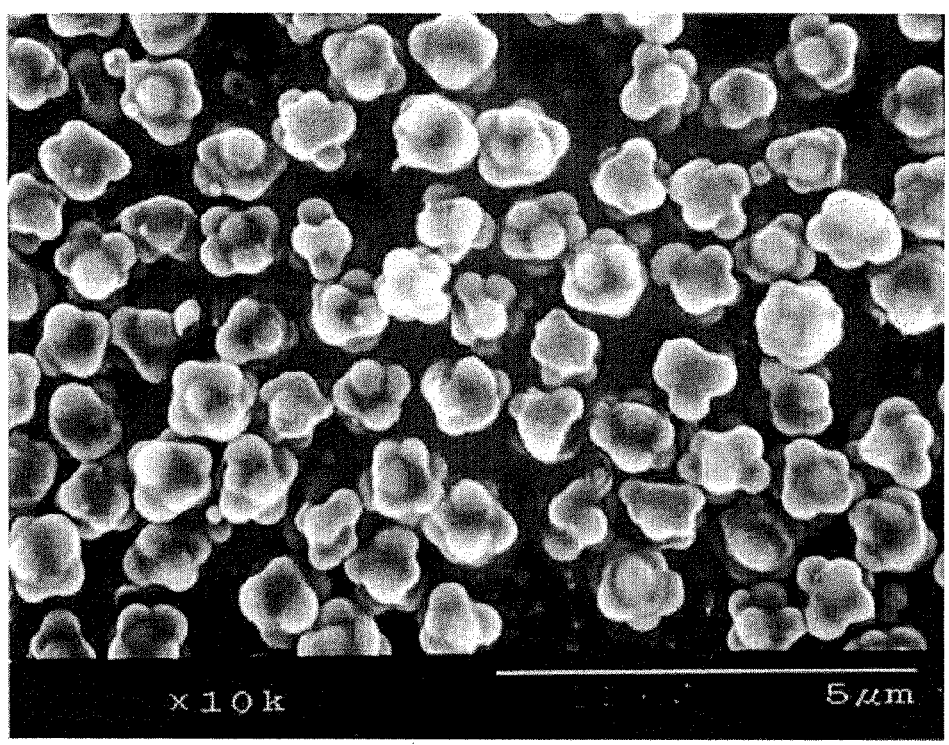
FIG. 4 is an electron micrograph of composite particles as obtained in Example 18.

The obtained white powders were 33.9 grams and observed under an electron microscope. The photograph of FIG. 4 shows sugar-plum-shaped particles having projections on surfaces of the particles. Particles of polymethylsilsesquioxane alone were hardly observed.

Example 19

Three hundred parts by weight of water were charged into a reaction vessel equipped with a thermometer, a reflux device and a stirrer, and loaded thereinto were 22.5 parts by weight of copolymer resin particles of polystyrene and polymethylmethacrylate with an average particle diameter of 1 μm (polystyrene to polymethacrylate=40 to 60). Ultrasonic waves were irradiated for 1 minute to obtain a resin particle dispersion liquid.

A liquid temperature of the dispersion liquid was set to be 30° C., and further added were 15 parts by weight of methyltrimethoxysilane to obtain a hydrolysate of methyltrimethoxysilane.

A 30-minute stirring was carried out by keeping the 30-degree Celsius liquid temperature, and quickly added were 10 parts by weight of 1 weight percent ammonia water. The stirring was stopped in 1 minute. A pH of such reaction liquid was 9.7 at this time.

Figure 5:
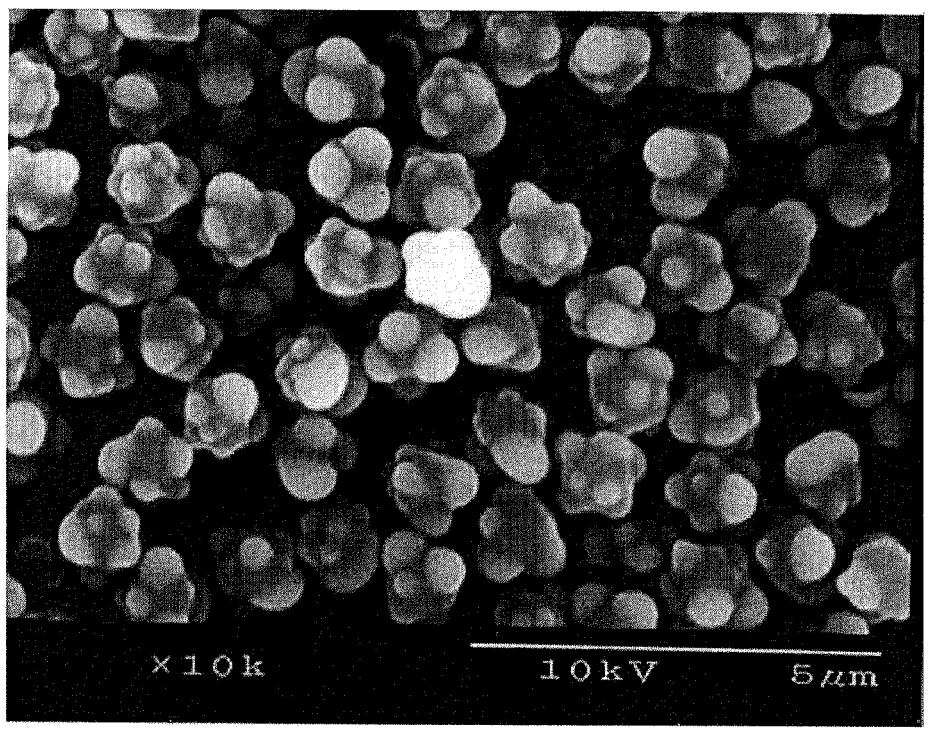
FIG. 5 is an electron micrograph of composite particles as obtained in Example 19.

Maturation was done for 10 hours in a still standing state, filtration and drying were carried out, and white powders were obtained. The obtained white powders were 29.0 grams and observed under an electron microscope. The photograph of FIG. 5 shows sugar-plum-shaped particles having projections on surfaces of the particles. Particles of polymethylsilsesquioxane alone were hardly observed.

Refractive indexes of the core particles can be set correspondingly to desired values by using the above-described copolymer resin particles, which may be actualized for use in art related to optics.

Example 20

Three hundred parts by weight of water were charged into a reaction vessel equipped with a thermometer, a reflux device and a stirrer, and loaded thereinto were 25 parts by weight of polymethylmethacrylate resin particles with an average particle diameter of 2 μm ("Art Pearl J-4P" made by Negami Chemical Industrial Company). Ultrasonic waves were irradiated for 1 minute to obtain a polymethylmethacrylate resin particle dispersion liquid.

Ten parts by weight of 1 weight percent ammonia water were quickly added and stirred well. A soft stirring was subsequently carried out.

A liquid temperature of the dispersion liquid was set to be 30° C., and dripped were 10 parts by weight of methyltrimethoxysilane over a period of 15 minutes. A 30-minute stirring was carried out, maturation was done for 10 hours in a still standing state, filtration and drying were carried out, and white powders were obtained. A pH of such reaction liquid was 9.7 at this time. By raw material charge ratios, polymethylsilsesquioxane was 20 parts by weight relative to 100 parts by weight of the polymethylmethacrylate resin particles.

Figure 6:
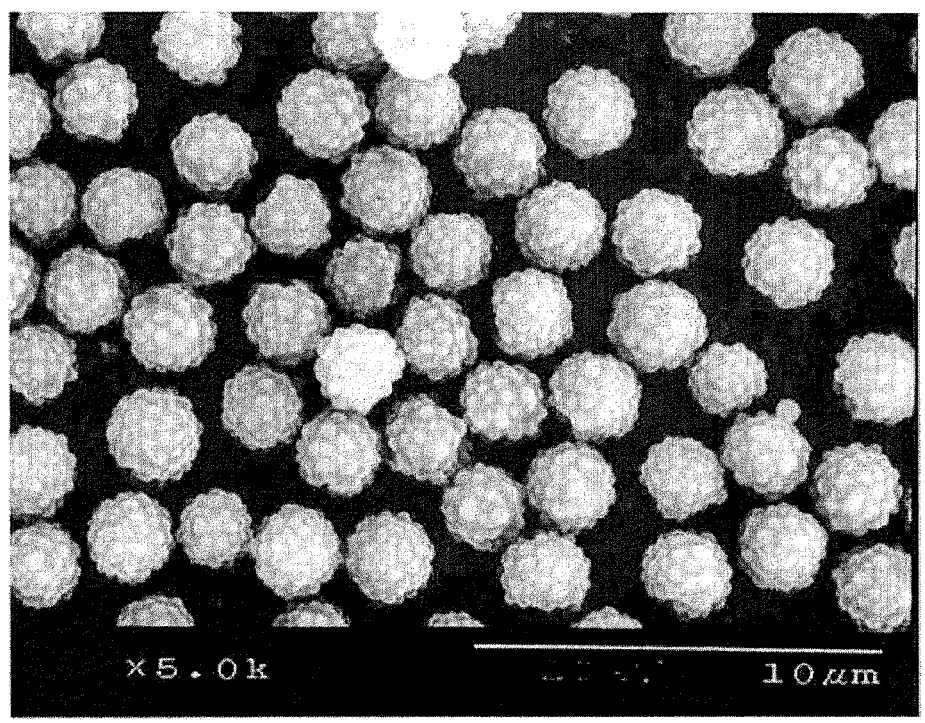
FIG. 6 is an electron micrograph of composite particles as obtained in Example 20.

The obtained white powders were 29.1 grams and observed under an electron microscope. The photograph of FIG. 6 shows sugar-plum-shaped particles having projections on surfaces of the particle. Particles of polymethylsilsesquioxane alone were hardly observed.

Comparative Example 1

Three hundred parts by weight of water were charged into a reaction vessel equipped with a thermometer, a reflux device and a stirrer, and loaded thereinto were 25 parts by weight of polymethylmethacrylate resin particles with an average particle diameter of 2 μm ("Art Pearl J-4P" made by Negami Chemical Industrial Company). Ultrasonic waves were irradiated for 1 minute to obtain a polymethylmethacrylate resin particle dispersion liquid.

A liquid temperature of the dispersion liquid was set to be 30° C., and further added were 4 parts by weight of methyltrimethoxysilane to obtain a hydrolysate of methyltrimethoxysilane in the polymethylmethacrylate resin particle dispersion liquid.

A 30-minute stirring was carried out by keeping the 30-degree Celsius liquid temperature, and quickly added were 10 parts by weight of 1 weight percent ammonia water. The stirring was stopped in 1 minute. A pH of such reaction liquid was 9.8 at this time.

Maturation was done for 10 hours in a still standing state, filtration and drying were carried out, and white powders were obtained. The obtained white powders were 26.3 grams.

By raw material charge ratios, polymethylsilsesquioxane was 8 parts by weight relative to 100 parts by weight of the polymethylmethacrylate resin particles.

Figure 7:
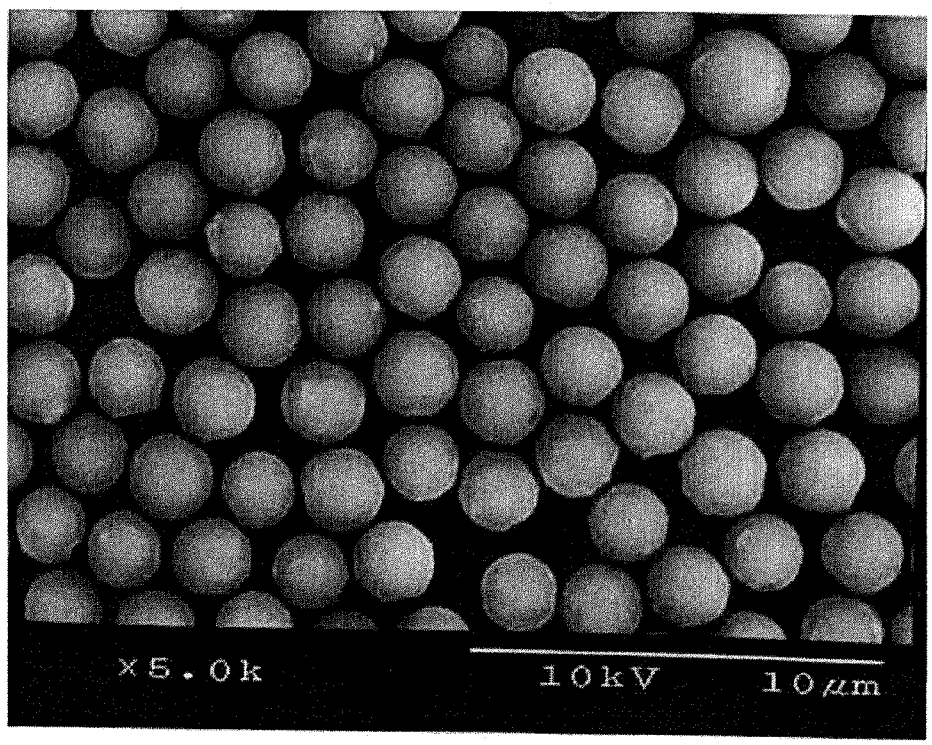
FIG. 7 is an electron micrograph of composite particles as obtained in Comparative Example 1.

The obtained white powders were observed under an electron microscope. Projections were not observed on surfaces of the particles and the particles were spherical particles coated uniformly with polymethylsilsesquioxane, as shown in the photograph of FIG. 7.

Comparative Example 2

Three hundred parts by weight of water were charged into a reaction vessel equipped with a thermometer, a reflux device and a stirrer, and loaded thereinto were 25 parts by weight of polymethylmethacrylate resin particles with an average particle diameter of 2 μm ("Art Pearl J-4P" made by Negami Chemical Industrial Company). Ultrasonic waves were irradiated for 1 minute to obtain a polymethylmethacrylate resin particle dispersion liquid.

Seven parts by weight of 28 weight percent ammonia water were quickly added and stirred well. A soft stirring was subsequently carried out.

A liquid temperature of the dispersion liquid was set to be 30° C., and dripped were 10 parts by weight of methyltrimethoxysilane over a period of 15 minutes. A 30-minute stirring was carried out. A pH of such reaction liquid was 10.8 at this time. Maturation was done for 10 hours in a still standing state, filtration and drying were carried out, and white powders were obtained. By raw material charge ratios, polymethylsilsesquioxane was 20 parts by weight relative to 100 parts by weight of the polymethylmethacrylate resin particles.

Figure 8:
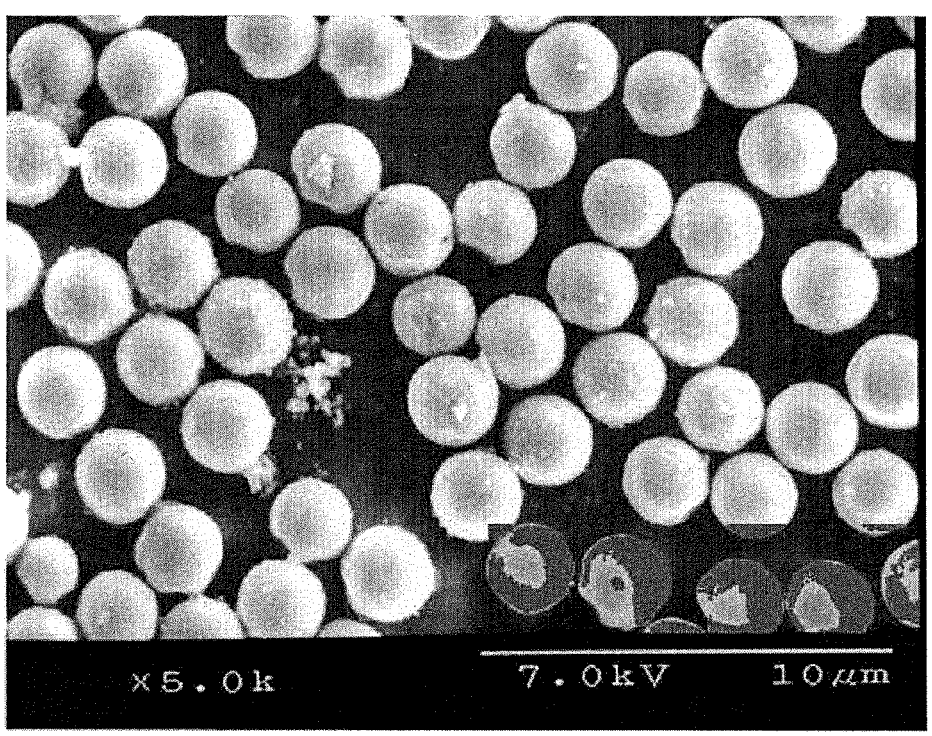
FIG. 8 is an electron micrograph of composite particles as obtained in Comparative Example 2.

The obtained white powders were 29.0 grams and observed under an electron microscope. Projections were not observed on surfaces of the particles and the particles were spherical particles coated uniformly with polymethylsilsesquioxane, as shown in the photograph of FIG. 8.

Ten panelists placed a small amount of each of the obtained powders of Example 8 and Comparative Example 2 to a back of their hands and spread the placed powders with a fingertip to evaluate slidability and extensibility of the obtained powders of Example 8 and Comparative Example 2. Ten persons out of the 10 persons found the obtained powders of Example 8 to be superior to those of Comparative Example 2 in slidability and extensibility.

Figures 9X, 9Y:
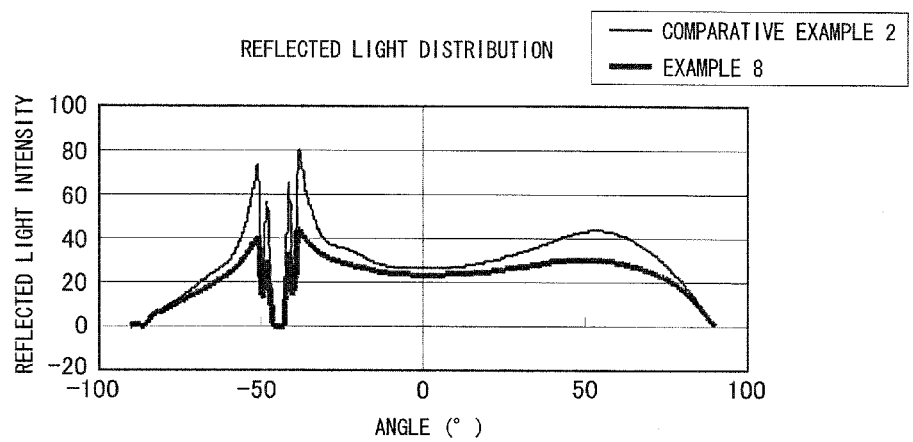
FIGS. 9X and 9Y are respectively a graph and a table of data by the measurement results of reflected light distributions of powders as obtained in Example 8 and Comparative Example 2 within a range of −90 to +90° for an incidence angle of −45°.

The obtained powders of Example 8 and Comparative Example 2 were used to measure reflected light distributions within a range of an angle of −90 to +90 degrees for an incidence angle of −45 degrees with a reflected light distribution measurement apparatus ("GP-200" made by Murakami Color Research Laboratory Company). The graph of FIG. 9 shows the measurement results. The obtained particles of Example 8 were found to be superior to the obtained particles of Comparative Example 2 in light diffusivity. Presumably, the light diffusivity was improved because the particles were sugar-plum shaped.

Diffusion plates with a thickness of 2 mm and 3 mm were prepared by adding the obtained powders of Example 8 at two levels of 0.2 weight percent and 0.5 weight percent to a polystyrene resin. Similarly, the obtained powders of Comparative Example 2 also were used to prepare such diffusion plates.

Figure 10:
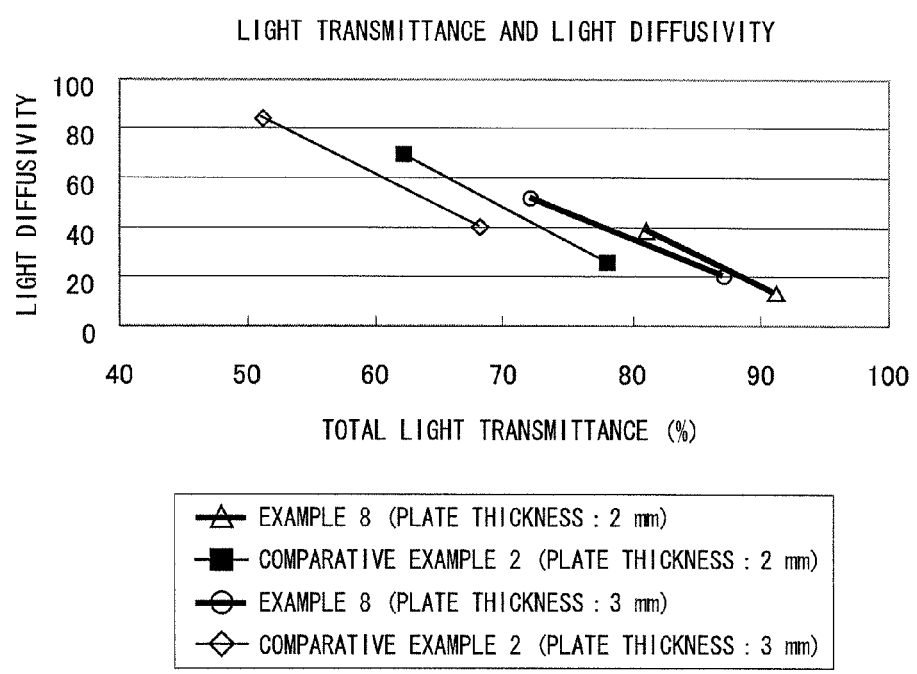
FIG. 10 is a graph of a relationship between total light transmittance and light diffusivity measured by using diffusion plates with a thickness of 2 mm and 3 mm formed by using the powders as obtained in Example 8 and Comparative Example 2.

Light transmittance and light diffusivity of the diffusion plates were measured, and the graph of FIG. 10 shows the measurement results. The obtained sugar-plum-shaped particles of Example 8 were found to be superior to the obtained spherical particles of Comparative Example 2 in light transmittance and diffusivity.

Example 21

Three hundred parts by weight of water were charged into a reaction vessel equipped with a thermometer, a reflux device and a stirrer, and loaded thereinto were 25 parts by weight of polymethylmethacrylate resin particles with an average particle diameter of 2 μm ("Art Pearl J-4P" made by Negami Chemical Industrial Company). Ultrasonic waves were irradiated for 1 minute to obtain a polymethylmethacrylate resin particle dispersion liquid.

Ten parts by weight of 1 weight percent ammonia water were quickly added and stirred well. A soft stirring was subsequently carried out.

A liquid temperature of the dispersion liquid was set to be 30° C., and dripped were 10 parts by weight of methyltrimethoxysilane over a period of 15 minutes. A 30-minute stirring was carried out, maturation was done for 10 hours in a still standing state, filtration and drying were carried out, and white powders were obtained. A pH of such reaction liquid was 9.7 at this time. By raw material charge ratios, polymethylsilsesquioxane was 20 parts by weight relative to 100 parts by weight of the polymethylmethacrylate resin particles.

Figure 11:
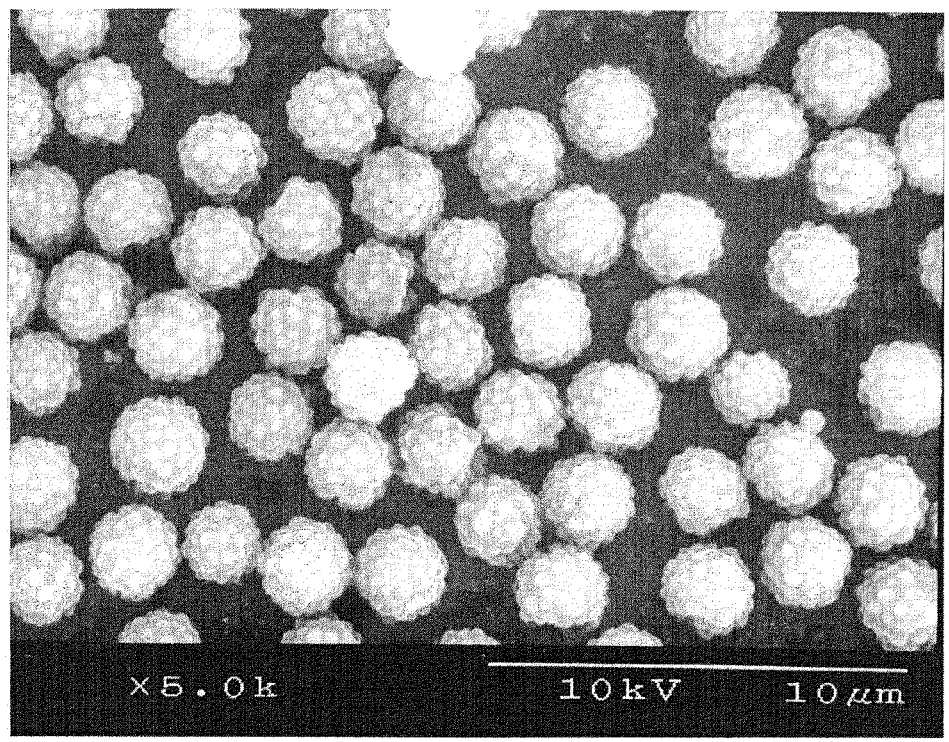
FIG. 11 is an electron micrograph of composite particles as obtained in Example 21.

The obtained white powders were 29.1 grams and observed under an electron microscope. The photograph of FIG. 11 shows sugar-plum-shaped particles having projections on surfaces of the particles. Particles of polymethylsilsesquioxane alone were hardly observed.

Examples 22 to 28

Sugar-plum-shaped particles were obtained as in Example 22 in the same manner as in Example 21 in addition to reaction temperatures as shown in Table 3 below.

Sugar-plum-shaped particles were obtained as in Examples 23 to 25 in the same manner as in Example 21 in addition to charging amounts as shown in Table 3 below.

Sugar-plum-shaped particles were obtained as in Examples 26 to 28 in the same manner as in Example 21 in addition to average particle diameters of acrylic spherical resin particles and charging amounts as shown in Table 3 below.

TABLE 3

| | Example 22 | Example 23 | Example 24 | Example 25 | Example 26 | Example 27 | Example 28 |
|---|---|---|---|---|---|---|---|
| Water (part by wt.) | 300 | 300 | 300 | 300 | 300 | 300 | 300 |
| Organic resin particles | J-4P | J-4P | J-4P | J-4P | J-7P | Acrylic | M-305 |
| Average particle diameters (μm) of organic resin particles | 2 | 2 | 2 | 2 | 7 | 1 | 5 |

TABLE 3-continued

|  | Example 22 | Example 23 | Example 24 | Example 25 | Example 26 | Example 27 | Example 28 |
|---|---|---|---|---|---|---|---|
| Additive amount of organic resin particles (part by wt.) | 25 | 19.5 | 26 | 16 | 30 | 20 | 30 |
| 1 weight % ammonia water (part by wt.) | 10 | 10 | 10 | 10 | 10 | 10 | 10 |
| Methyltrimethoxysilane (part by wt.) | 10 | 22 | 8 | 28 | 15 | 15 | 15 |
| Reaction temperatures during dehydration condensation (° C.) | 50 | 20 | 20 | 20 | 30 | 20 | 20 |
| Shape of synthesized particles | Sugar-plum-shaped | Sugar-plum-shaped | Sugar-plum-shaped | Sugar-plum-shaped | Sugar-plum-shaped | Sugar-plum-shaped | Sugar-plum-shaped |
| Width of projections (μm) | 0.4 | 0.6 | 0.2 | 0.6 | 0.3 | 0.3 | 0.3 |
| Average particle diameters of synthesized particles (μm) | 2.3 | 2.5 | 2.2 | 2.8 | 7.3 | 1.2 | 5.4 |

Example 29

Three hundred parts by weight of water were charged into a reaction vessel equipped with a thermometer, a reflux device and a stirrer, and loaded thereinto were 22 parts by weight of polystyrene resin particles with an average particle diameter of 3 μm. Ultrasonic waves were irradiated for 1 minute to obtain a polystyrene resin particle dispersion liquid.

Ten parts by weight of 1 weight percent ammonia water were quickly added and stirred well. A soft stirring was subsequently carried out.

A liquid temperature of the dispersion liquid was set to be 30° C., and dripped were 9 parts by weight of methyltrimethoxysilane over a period of 5 minutes. A 20-minute stirring was carried out, maturation was done for 2 hours in a still standing state, filtration and drying were carried out, and white powders were obtained. A pH of such reaction liquid 9.6 at this time. By raw material charge ratios, polymethylsilsesquioxane was 20 parts by weight relative to 100 parts by weight of the polystyrene resin particles.

Figure 12:
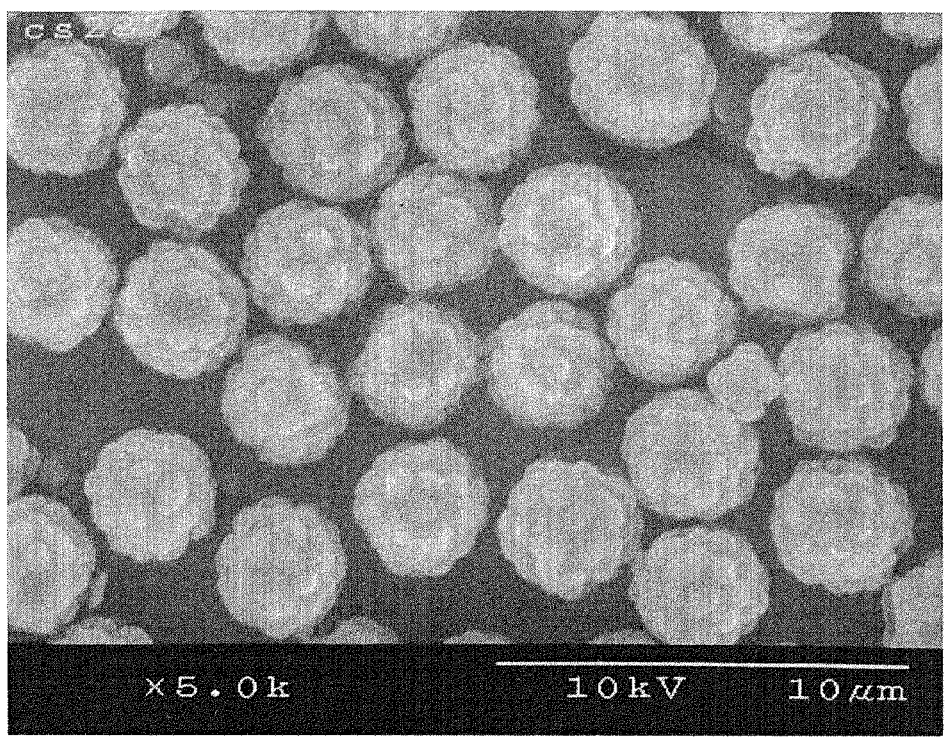
FIG. 12 is an electron micrograph of composite particles as obtained in Example 29.

The obtained white powders were 25.9 grams and observed under an electron microscope. The photograph of FIG. 12 shows sugar-plum-shaped particles having projections on surfaces of the particles. Particles of polymethylsilsesquioxane alone were hardly observed.

Example 30

Three hundred parts by weight of water were charged into a reaction vessel equipped with a thermometer, a reflux device and a stirrer, and loaded thereinto were 22.5 parts by weight of polyurethane resin particles with an average particle diameter of 7 μm ("Art Pearl C-800" (transparent) made by Negami Chemical Industrial Company). Ultrasonic waves were irradiated for 1 minute to obtain a polyurethane resin particle dispersion liquid.

Ten parts by weight of 1 weight percent ammonia water were quickly added and stirred well. A soft stirring was subsequently carried out.

A liquid temperature of the dispersion liquid was set to be 30° C., and dripped were 15 parts by weight of methyltrimethoxysilane over a period of 5 minutes. A 20-minute stirring was carried out, maturation was done for 2 hours in a still standing state, filtration and drying were carried out, and white powders were obtained. A pH of such reaction liquid was 9.6 at this time. By raw material charge ratios, polymethylsilsesquioxane was 33 parts by weight relative to 100 parts by weight of the polyurethane resin particles.

Figure 13:
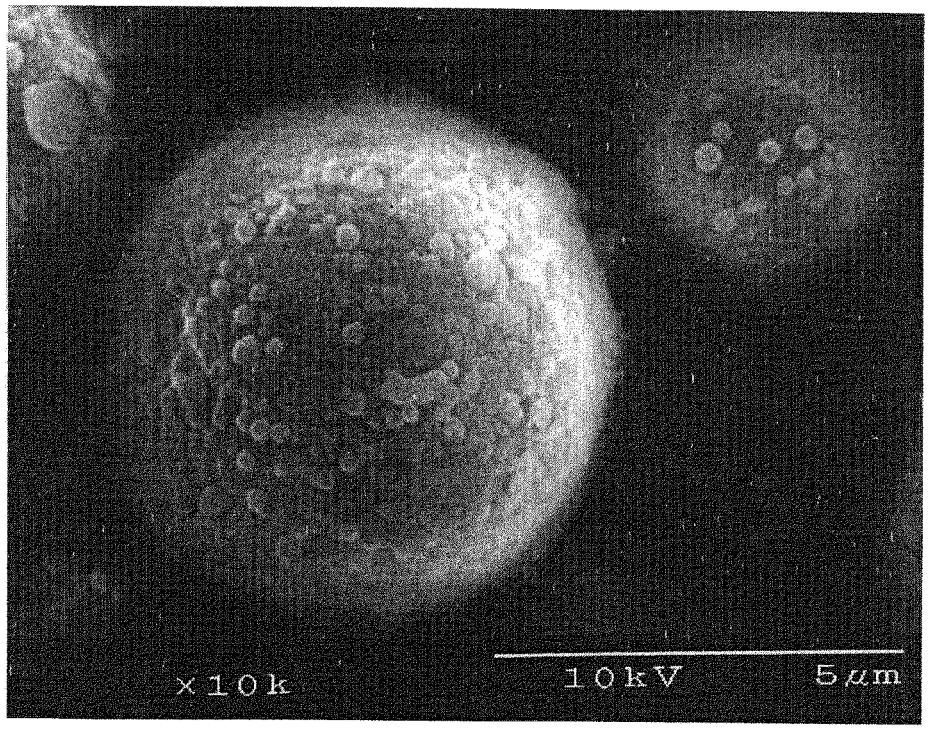
FIG. 13 is an electron micrograph of composite particles as obtained in Example 30.

The obtained white powders were 28.9 grams and observed under an electron microscope. The photograph of FIG. 13 shows sugar-plum-shaped particles having projections on surfaces of the particles. Particles of polymethylsilsesquioxane alone were hardly observed.

Example 31

Three hundred parts by weight of water were charged into a reaction vessel equipped with a thermometer, a reflux device and a stirrer, and added thereto were 10 parts by weight of 1 weight percent ammonia water to prepare an aqueous ammonia solution. Into the aqueous ammonia solution were loaded 25 parts by weight of "Art Pearl J-5P" acrylic spherical resin particles made by Negami Chemical Industrial Company. Ultrasonic waves were irradiated for 1 minute to obtain an acrylic resin particle dispersion liquid.

A liquid temperature of the dispersion liquid was set to be 30° C., and added were 10 parts by weight of methyltrimethoxysilane over a period of 1 minute while being stirred gently. A 20-minute stirring was successively carried out by keeping the 30-degree Celsius liquid temperature, which was then stopped.

Figure 14:
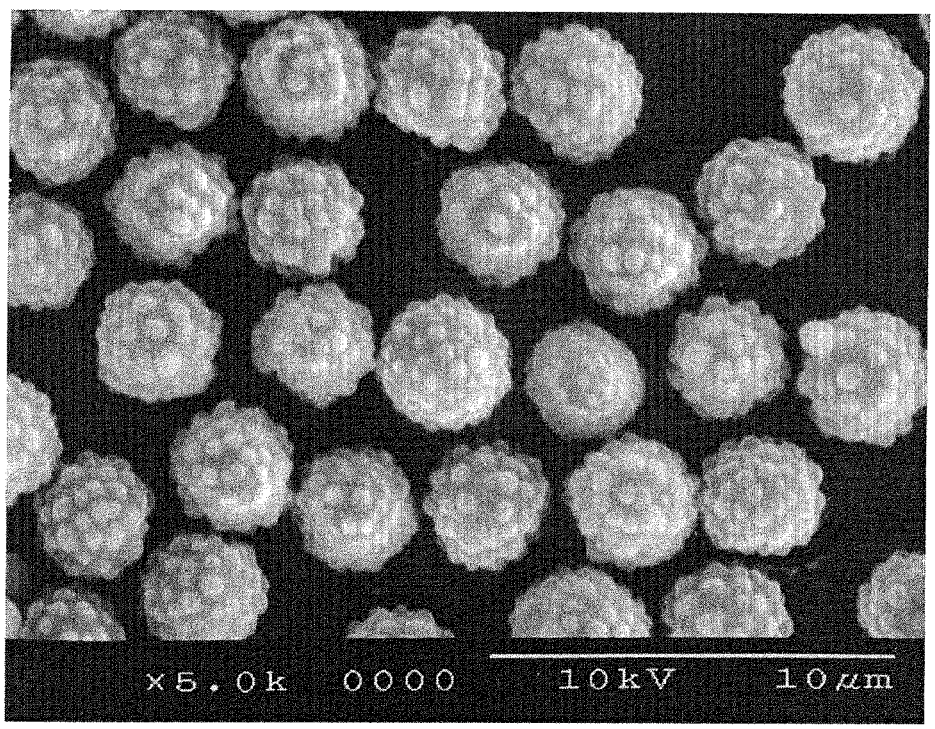
FIG. 14 is an electron micrograph of composite particles as obtained in Example 31.

Maturation was done for 2 hours in a still standing state, filtration and drying were carried out, and white powders were obtained. The obtained white powders were 28.9 grams and observed under an electron microscope. The photograph of FIG. 14 shows sugar-plum-shaped particles having projections on surfaces of the particles. Particles of polymethylsilsesquioxane alone were hardly observed.

Examples 32 to 38

Sugar-plum-shaped particles were obtained as in Example 32 in the same manner as in Example 21 in addition to reaction temperatures as shown in Table 4 below.

Sugar-plum-shaped particles were obtained as in Examples 33 and 34 in the same manner as in Example 21 in addition to charging amounts as shown in Table 4 below.

Sugar-plum-shaped particles were obtained as in Examples 35 and 36 in the same manner as in Example 21 in addition to average particle diameters of acrylic spherical resin particles and charging amounts as shown in Table 4 below.

Sugar-plum-shaped particles were obtained as in Examples 37 and 38 in the same manner as in Example 21 in addition to organic resin particles as shown in Table 4 below.

TABLE 4

|  | Example 32 | Example 33 | Example 34 | Example 35 | Example 36 | Example 37 | Example 38 |
|---|---|---|---|---|---|---|---|
| Water (part by wt.) | 300 | 300 | 300 | 300 | 300 | 300 | 300 |
| 1 weight % ammonia water (part by wt.) | 10 | 10 | 10 | 10 | 10 | 10 | 10 |
| Organic resin particles | J-5P | J-5P | J-5P | J-7P | Acrylic | Polystyrene | C-800 |
| Average particle diameters ($\mu$m) of organic resin particles | 3 | 3 | 3 | 7 | 1 | 3 | 7 |
| Additive amount of organic resin particles (part by wt.) | 25 | 19.5 | 26 | 30 | 20 | 22 | 22.5 |
| Methyltrimethoxysilane (part by wt.) | 10 | 22 | 8 | 15 | 15 | 9 | 15 |
| Reaction temperatures during dehydration condensation (° C.) | 50 | 20 | 20 | 30 | 20 | 30 | 30 |
| Shape of synthesized particles | Sugar-plum-shaped | Sugar-plum-shaped | Sugar-plum-shaped | Sugar-plum-shaped | Sugar-plum-shaped | Sugar-plum-shaped | Sugar-plum-shaped |
| Width of projections ($\mu$m) | 0.4 | 0.5 | 0.3 | 0.3 | 0.3 | 0.6 | 0.2 |
| Average particle diameters of synthesized particles ($\mu$m) | 3.4 | 3.6 | 3.4 | 7.4 | 1.2 | 3.5 | 7.1 |

Example 39

Three hundred parts by weight of water were charged into a reaction vessel equipped with a thermometer, a reflux device and a stirrer, and loaded thereinto were 25 parts by weight of polymethylmethacrylate resin particles with an average particle diameter of 2 $\mu$m ("Art Pearl J-4P" made by Negami Chemical Industrial Company). Ultrasonic waves were irradiated for 1 minute to obtain a polymethylmethacrylate resin particle dispersion liquid.

A liquid temperature of the dispersion liquid was set to be 30° C., and further added were 8 parts by weight of methyltrimethoxysilane and 2 parts by weight of dimethyldimethoxysilane to obtain each hydrolysate of methyltrimethoxysilane and dimethyldimethoxysilane in the polymethylmethacrylate resin particle dispersion liquid. A 30-minute stirring was carried out by keeping the 30-degree Celsius liquid temperature. Five parts by weight of 1 weight percent ammonia water were quickly added, and the stirring was stopped in 1 minute. A pH of such reaction liquid was 9.1 at this time. Maturation was done for 5 hours in a still standing state, filtration and drying were carried out, and white powders were obtained.

Figure 15:
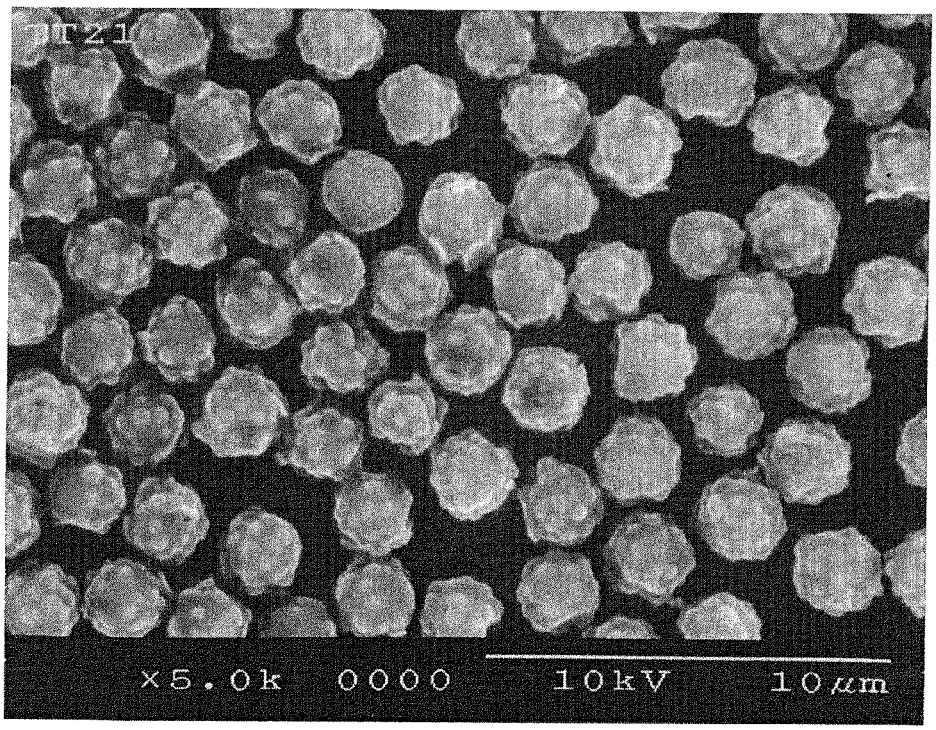
FIG. 15 is an electron micrograph of composite particles as obtained in Example 39.

The obtained white powders were observed under an electron microscope. The photograph of FIG. 15 shows sugar-plum-shaped particles having projections on surfaces of the particles. Particles of polymethylsiloxane alone were hardly observed.

Example 40

White powders were obtained under the same conditions as in Example 39 in addition to 6 parts by weight of methyltrimethoxysilane and 4 parts by weight of trimethylmonomethoxysilane as organoalkoxysilane.

Figure 16:
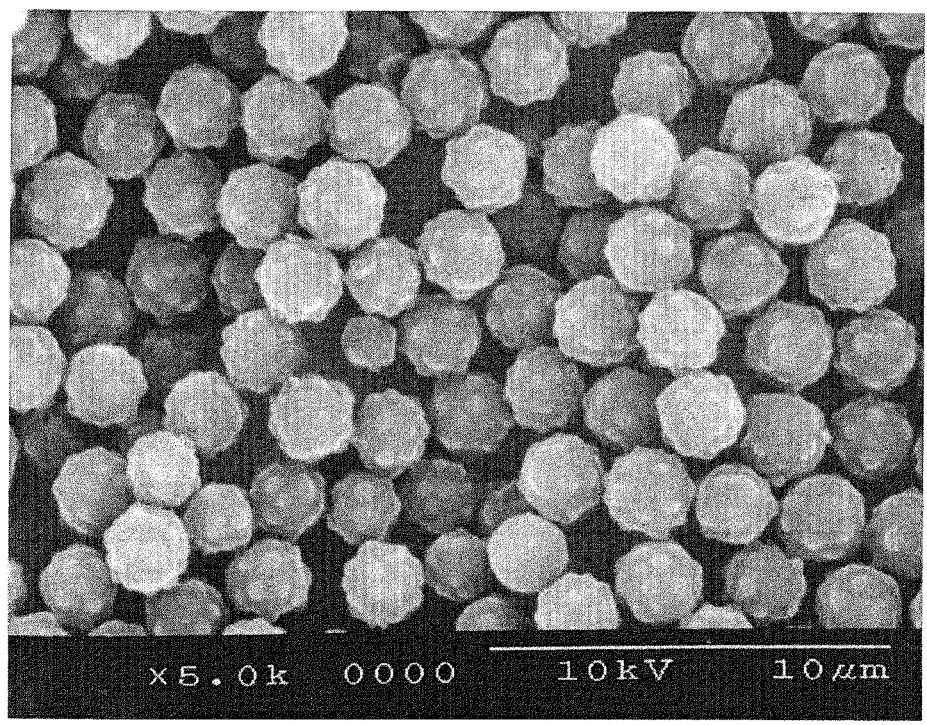
FIG. 16 is an electron micrograph of composite particles as obtained in Example 40.

The obtained powders were observed under an electron microscope. The photograph of FIG. 16 shows sugar-plum-shaped particles having projections on surfaces of the particles. Particles of polymethylsiloxane alone were hardly observed.

Example 41

White powders were obtained under the same conditions as in Example 39 in addition to 9 parts by weight of methyltrimethoxysilane and 1 part by weight of tetramethoxysilane as organoalkoxysilane.

Figure 17:
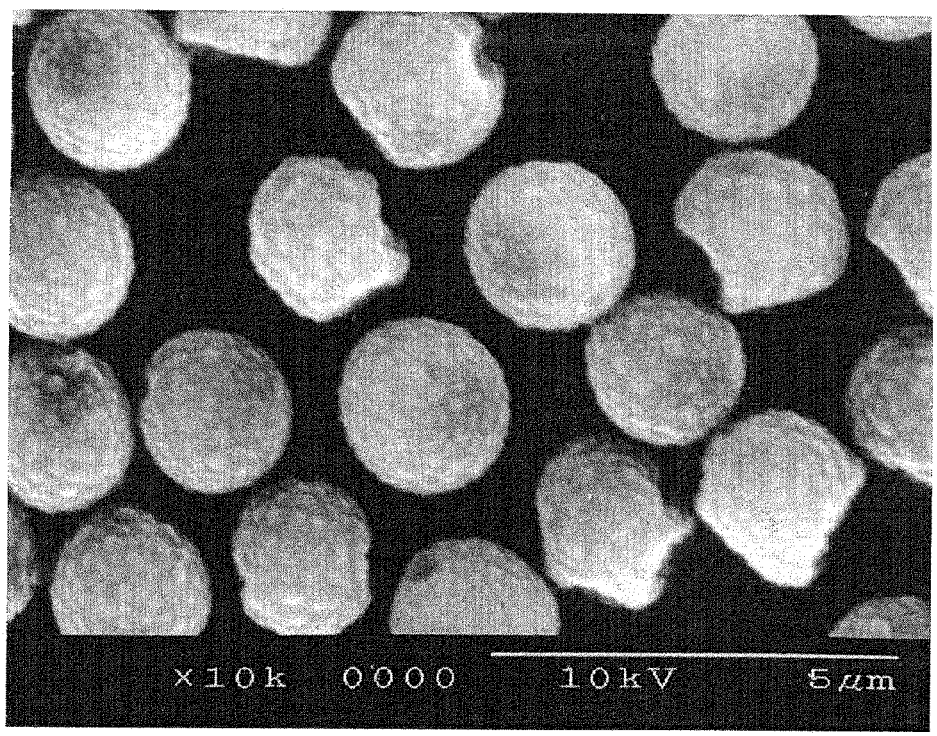
FIG. 17 is an electron micrograph of composite particles as obtained in Example 41.

The obtained white powders were observed under an electron microscope. The photograph of FIG. 17 shows sugar-plum-shaped particles having projections on surfaces of the particles. Particles of polymethylsiloxane alone were hardly observed.

Example 42

White powders were obtained under the same conditions as in Example 39 in addition to 7 parts by weight of methyltrimethoxysilane, 1 part by weight of dimethyldimethoxysilane, and 2 parts by weight of trimethylmonomethoxysilane as organoalkoxysilane.

Figure 18:
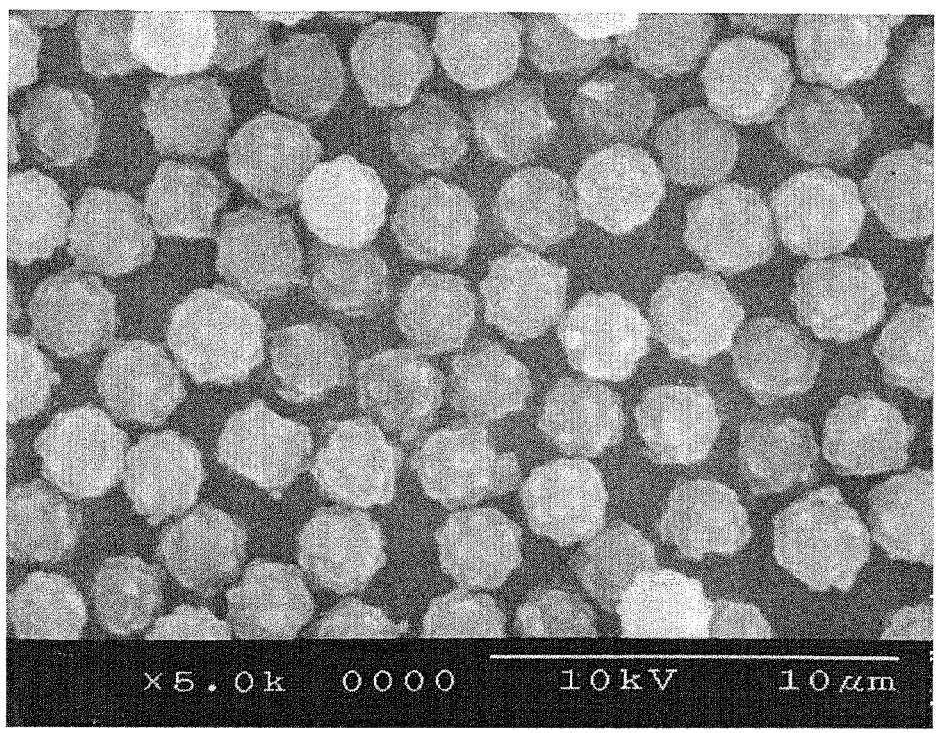
FIG. 18 is an electron micrograph of composite particles as obtained in Example 42.

The obtained powders were observed under an electron microscope. The photograph of FIG. 18 shows sugar-plum-shaped particles having projections on surfaces of the particles. Particles of polymethylsiloxane alone were hardly observed.

Example 43

White powders were obtained under the same conditions as in Example 39 in addition to 9.5 parts by weight of methyltrimethoxysilane as organoalkoxysilane and 0.5 parts by weight of methyltrichlorosilane as organohalosilane.

Figure 19:
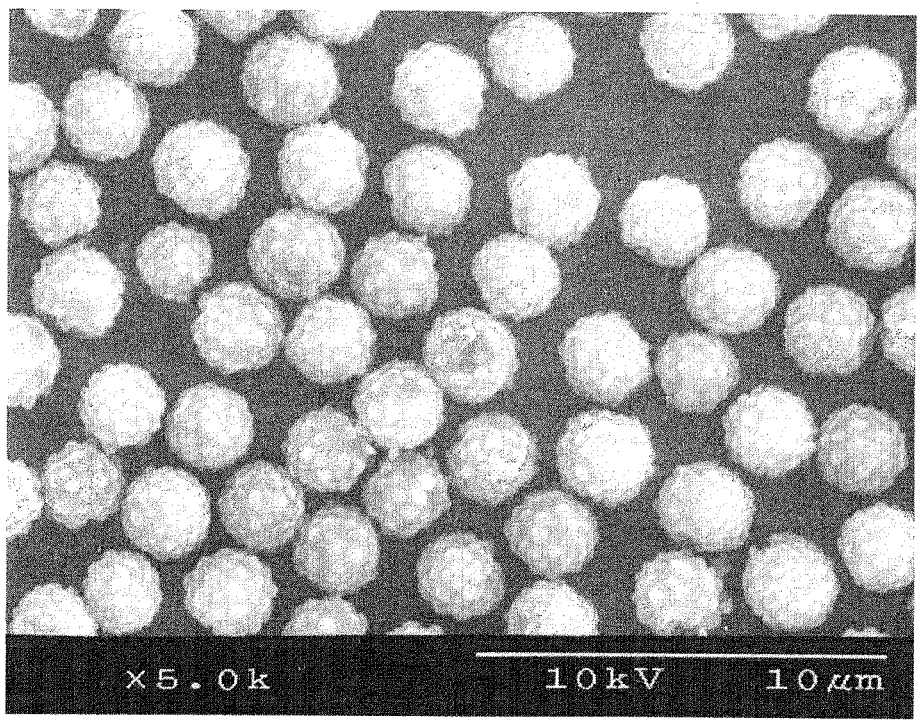
FIG. 19 is an electron micrograph of composite particles as obtained in Example 43.

The obtained white powders were observed under an electron microscope. The photograph of FIG. 19 shows sugar-plum-shaped particles having projections on surfaces of the particles. Particles of polymethylsilsesquioxane alone were hardly observed.

Example 44

Three hundred parts by weight of water were charged into a reaction vessel equipped with a thermometer, a reflux device and a stirrer, and loaded thereinto were 25 parts by weight of polymethylmethacrylate resin particles with an average particle diameter of 2 $\mu$m ("Art Pearl J-4P" made by Negami Chemical Industrial Company). Ultrasonic waves were irradiated for 1 minute to obtain a polymethylmethacrylate resin particle dispersion liquid. Five parts by weight of 1 weight percent ammonia water were quickly added and stirred well. A soft stirring was subsequently carried out.

A liquid temperature of the dispersion liquid was set to be 30° C., and further added were 15 parts by weight of methyltrimethoxysilane. A soft stirring was subsequently carried out in a state where the dispersion liquid and methyltrimethoxysilane were separated in two layers. The methyltrimethoxysilane layer substantially disappeared in 6 minutes from the addition of methyltrimethoxysilane. A 10-minute stirring was carried out, maturation was done for 2 hours in a still standing state, filtration and drying were carried out, and white powders were obtained.

Figure 20:
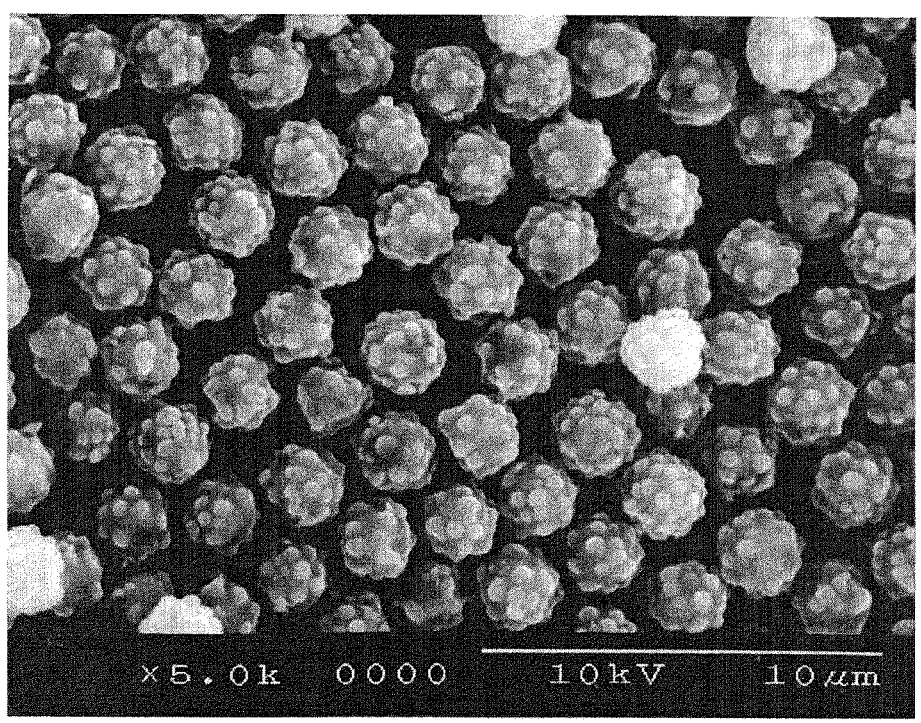
FIG. 20 is an electron micrograph of composite particles as obtained in Example 44.

The obtained white powders were observed under an electron microscope. The photograph of FIG. 20 shows sugar-plum-shaped particles having projections on surfaces of the particles. Particles of polymethylsilsesquioxane alone were hardly observed.

Methyltrimethoxysilane is separated from the dispersion liquid into two layers because methyltrimethoxysilane is water-insoluble. When a hydrolysis reaction of methyltrimethoxysilane progresses at an interface, a water-soluble hydrolysate disperses into the dispersion liquid, and a dehydration condensation reaction occurs so as to synthesize sugar-plum-shaped particles.

Example 45

Three hundred parts by weight of water were charged into a reaction vessel equipped with a thermometer, a reflux device and a stirrer, and added thereto were 12 parts by weight of methyltrimethoxysilane. One hour stirring was carried out at 30° C. to prepare a methyltrimethoxysilane hydrolysate solution.

Then loaded into the hydrolysate solution were 25 parts by weight of polymethylmethacrylate resin particles with an average particle diameter of 3 μm ("Art Pearl J-5P" made by Negami Chemical Industrial Company). Ultrasonic waves were irradiated for 1 minute to obtain an acrylic resin particle dispersion liquid. A liquid temperature of the dispersion liquid was set to be 30° C., and 5 parts by weight of 1 weight percent ammonia water were added while being stirred. One minute stirring was carried out, maturation was done for 2 hours in a still standing state, filtration and drying were carried out, and white powders were obtained.

Figure 21:
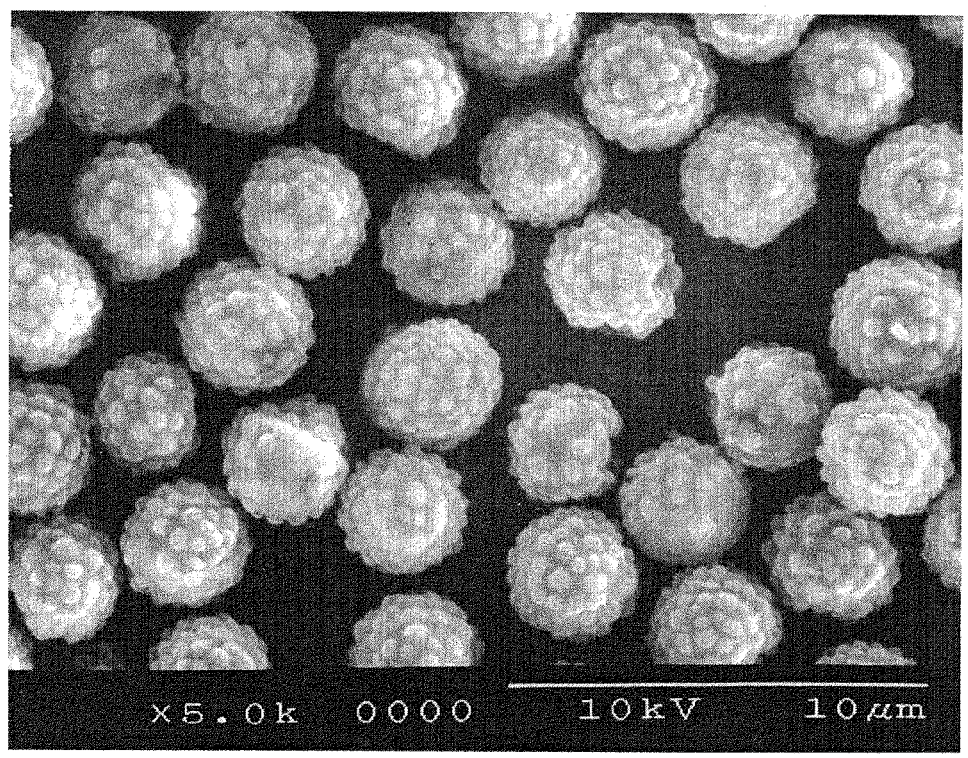
FIG. 21 is an electron micrograph of composite particles as obtained in Example 45.

The obtained white powders were observed under an electron microscope. The photograph of FIG. 21 shows sugar-plum-shaped particles having projections on surfaces of the particles. Particles of polymethylsilsesquioxane alone were hardly observed.

The present invention relates to a process for producing sugar-plum-shaped particles having polyorganosiloxane projections on surfaces of organic resin particles that serve as cores. Such composite particles with sugar-plum-shape surfaces produced by this production process are industrially applicable as an agent imparting slidability, wear resistance, anti-blocking property, water repellency, light diffusivity, etc., to various plastics and rubbers, and such products as cosmetics.

What is claimed is:

1. A process for producing the sugar-plum-shaped particles, wherein the process consists of dispersing 10 to 100 parts by weight of an organotrialkoxysilane and/or an organotrialkoxysilane hydrolysate and 100 parts by weight of organic resin particles in water to form a reaction solution,
   then, before the organotrialkoxysilane and/or an organotrialkoxysilane hydrolysate undergoes a dehydration condensation reaction,
   adjusting the pH of the reaction solution to 8.0 to 10.5 by adding an alkaline substance or an alkaline aqueous solution to the reaction solution, and then
   precipitating particles having polyorganosiloxane projections on surfaces of the organic resin particles.

2. A process for producing sugar-plum-shaped particles consisting of:
   dispersing organic resin particles in water and adjusting the pH to 8.0 to 10.5 by adding an alkaline substance or an alkaline aqueous solution; then,
   adding drop-wise 10 to 100 parts by weight of an organotrialkoxysilane and/or an organotrialkoxysilane hydrolysate to 100 parts by weight of the organic resin particles; and then
   precipitating particles having polyorganosiloxane projections on surfaces of the organic resin particles.

3. The process of claim 2, wherein the organic resin particles are selected from the group consisting of polymethylmethacrylate resin particles, polystyrene resin particles, polyurethane resin particles, and acrylic resin particles.

4. The process of claim 2, wherein the organotrialkoxysilane and/or an organotrialkoxysilane hydrolysate is added over the course of about 1 to 15 minutes.

5. A process for producing sugar-plum-shaped particles consisting of:
   dispersing organic resin particles in water and adjusting the pH to 8.0 to 10.5 by adding an alkaline substance or an alkaline aqueous solution; then,
   adding 10 to 100 parts by weight of a water-insoluble organotrialkoxysilane to the 100 parts of the dispersed organic resin particles in water, thereby forming two layers;
   softly stirring the two layers until the water-insoluble layer disappears; and
   precipitating particles having polyorganosiloxane projections on surfaces of the organic resin particles.

6. The process of claim 5, wherein the water-insoluble organotrialkoxysilane is methyltrimethoxysilane.

* * * * *